United States Patent [19]
Kobayashi et al.

[11] 4,177,574
[45] Dec. 11, 1979

[54] METHOD AND APPARATUS FOR GRANULATING HYDRATED MATERIALS INCLUDING FOOD STUFFS

[75] Inventors: Masakazu Kobayashi, Tokyo; Koh Harashima, Kawaguchi, both of Japan

[73] Assignee: Kanesa Miso Kabushiki-Kaisha, Tokyo, Japan

[21] Appl. No.: 885,796

[22] Filed: Mar. 13, 1978

[30] Foreign Application Priority Data

Mar. 12, 1977 [JP]  Japan .................................. 52/27496

[51] Int. Cl.² .............................................. F26B 7/00
[52] U.S. Cl. .......................................... 34/12; 34/15; 34/92
[58] Field of Search ................................ 34/12, 15, 92

[56] References Cited
U.S. PATENT DOCUMENTS

| 2,386,052 | 10/1945 | Lundy | 34/92 |
| 3,566,612 | 3/1971 | Eilenberg et al. | 34/92 |

Primary Examiner—John J. Camby

[57] ABSTRACT

Hydrated materials such as bean paste are controlled as to their moisture content to an intermediate moisture content such as 12% to 40% on dry basis and higher than their plastic limit, and are then extruded into strips under vacuum, followed by the granulation of said strips under vacuum by applying thereto mechanical shearing force to produce granules of desired sizes.

4 Claims, 1 Drawing Figure

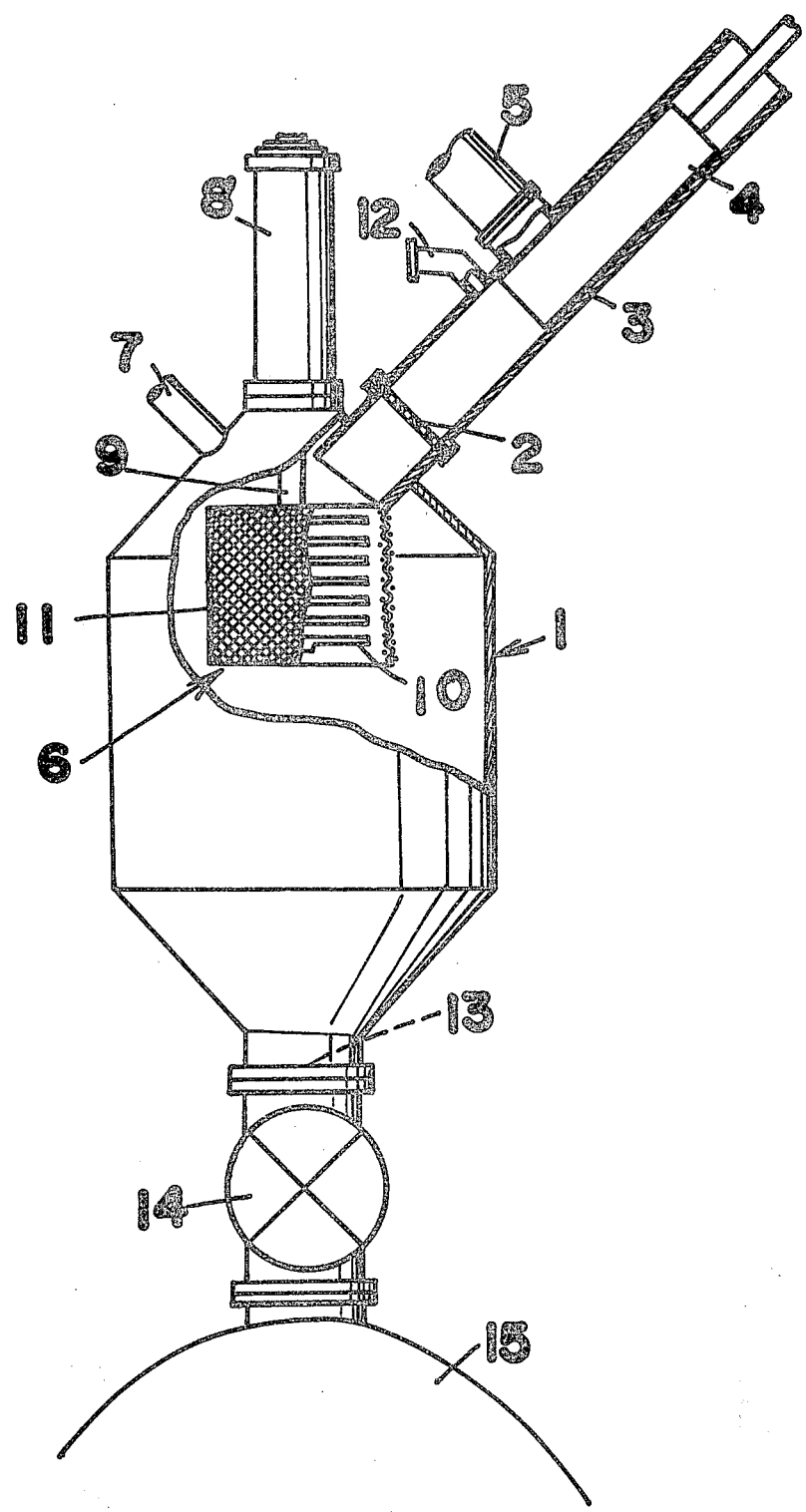

METHOD AND APPARATUS FOR GRANULATING HYDRATED MATERIALS INCLUDING FOOD STUFFS

This invention relates to a method for granulating materials which contain liquid constituents such as water and organic solvents including alcohols and others, and it relates also to an apparatus for such granulating.

It is a principal object of this invention to provide such method and apparatus, by which degeneration of the materials due to excessive compression, internal friction, pulverization and other operational factors accompanied to the granulation is lessened or eliminated, whereby granules of better qualities are obtainable.

Since granules prepared to desired sizes are easy to handle, compared to other forms such as solutions, pastes, lumps, powders and so on, various kinds of food stuffs, and medical and chemical materials have been granulated, or are tried to be granules.

Conventional methods for granulating materials of the aforementioned kind always need a step of drying the materials for reducing their moisture contents to a range lower than a plastic limit of the materials. The plastic limit of a material means that a lower-most moisture content with which the material can have plasticity, such lower-most moisture content in case of food stuffs being generally several percent to 20% on absolute dry basis (percentages hereinafter appeared are on dry basis, unless otherwise defined). Thus partly dried materials are granulated either by (1) being crushed by mechanical shocks or agitations, (2) being extruded through a perforated plate, or by (3) pulverizing the materials by having them further dried to a lower moisture content with which the materials can be pulverized and which is lower than several % and about monomolecular adsorption phase, and then flocculating pulverized materials by increasing their moisture content from polymolecular adsorption phase to a plastic phase by means of the humidification through water spraying thereupon and so on, and drying the flocculated materials. The reason why pre-drying or the reduction of moisture contents is required in these conventional methods is that when materials having a high moisture content are granulated, granules produced thereby shall be adhered to each other on account of high moisture, or shall be coagulated to blocks or mass, not being able to keep their granular forms. In addition, the above-mentioned conventional methods respectively have drawbacks. To wit, in case of the method mentioned in the above as (1), the distribution of granule sizes becomes large and uneven, and only p part of the product is marketable or utilizable when granules of even sizes are required. In case of the aforementioned method (2), materials have to be provided with a high viscosity and to be extruded under a high pressure, whereby certain materials will be degraded under such compression. In case of the conventional method (3), while a comparatively narrow distribution of differences of granular sizes can be assured, certain materials will be degraded or degenerated by mechanical pulveration operations, and particularly by the rehumidification and post-drying.

A drawback common to the above three conventional methods is that compared to time required for drying materials after granulation, the drying of materials prior to granulation takes a longer period of time, partly because granules have larger contact surfaces for drying, while materials such as a plate or block have less contact surfaces.

Besides the aforementioned conventional granulation methods, there are known a spray granulation method, and another method in which frozen materials are crushed and then dried. In the former method, the selection of granule sizes is limited to comparatively small ones, and it is not economical to dry granules which contain an excessive water content on account of the fact that the starting materials have to contain extremely high moisture content in order to be sprayed out. On the other hand, the latter method has such drawback that it can not be employed for granulating such materials, freezing temperature of which is extremely high.

In the present invention, its method comprised a step of extruding through perforations in strip-forms such materials having an intermediate moisture content which is higher than their plastic limits, and with which the materials keep softness sufficient enough for extrusion molding. Said intermediate moisture content means in other words that water is not only adsorbed to monomolecules and polymolecules, but also exists at such content which is higher than a plastic limit but can not constitute a gree solution, while water presents in the material structures, being bound to a certain extent by capillary condensation. This intermediate moisture content is higher than ten-odd % on dry basis and up to thirty-odd % in case of general food stuffs, and its water activity is about 0.65 AW to about 0.85 AW. Materials having the aforementioned intermediate moisture range do not require a high pressure when they are extruded, whereby degeneration of materials such as liberation of fatty substances from the materials accompanied to compression is avoided, and granules of desired even sizes are obtainable without thermal degeneration producible by a heat due to internal friction of materials.

This invention method comprises an additional novel step which is to extrude the materials into a chamber, vacuum of which is kept at a degree lower than a pressure which has a boiling point low enough to allow the extruded materials to keep their extruded forms and configurations and also low enough to assure the prevention of adhesion of extruded materials to each other. The extrusion of materials kept under vacuum has advantages that water contents of the materials extruded into strips decrease by the rapid evaporation of the water contents on account of vacuum, and that cooling effects due to vacuum can instantly harden the materials to such hardness under which they can keep their extruded forms and the adhesion of materials to each other shall not be occurred.

The present invention is further characterized by a step of granulating the materials extruded to strips and hardened in the second step by means of mechanical crushing such as agitation, cutting and hammering under vacuum of the aforementioned conditions.

Thus, in this invention, a series of operations from extrusion to granulation of materials can be made continuously as well as readily. It shall be noted also that as the extruded materials are kept at a low temperature under vacuum, oxidation of outer surfaces of granules and browning thereof are prevented. It shall be noted further that in this invention, it is readily possible to store obtained granules under vacuum, and also easily possible to transfer the granules to another drying chamber under vacuum without loosing vacuum of the both chambers.

In brief, this invention is afforded with four remarkable advantages, viz., (1) prevention of degeneration companied to granulation, (2) free selection of granule sizes by employment of perforations of a desired size, (3) even distribution of granule sizes without contamination of pulverized materials, yield being mearly 100%, and (4) as the drying of the materials before granulation is nominal and the drying of the materials is effected after they have been made to granules which are advantageous for drying, as above-mentioned, because they can have larger outer contact surfaces, expenses or costs for drying operations being largely reduced.

The working principle of this invention which is based upon behaviours and physical properties common to water contents or constituents contained in hydrophilic materials including food stuffs, is widely utilizable, for example, for granulating bean paste, condensed seasoning extracts, wheat gluten, other pastes, and other mushy and hydrophilic materials. Granules obtained in accordance with this invention can be used at a low temperature as they are granulated with a specific moisture content, or can be used as dried granules by drying or reducing further their water contents.

Examples of this invention will be described hereinafter with respect of granulating bean paste which is one of most popular food stuffs in Japan and which has been hardly been granulated without degeneration, with reference to the accompanying drawing which shows a partly cut-out side view of an apparatus for performing the present invention.

While moisture contents of bean paste can be 100% on dry basis and 50% on wet basis, it has no solvent-like liquid phase water content if its moisture content is lower than about 8 to 12% and its water activity is lower than 0.6 AW, while it can have free and continuous liquid solution, if its moisture content is more than 40%. In an intermediate area between the above-mentioned two moisture contens, viz., an area between about 12% to 40%, bean paste can have the intermediate moisture content, in which a certain amount of water exists in a liquid phase, being bound by capillary condensation.

If bean paste having a moisture content of thirty-odd % is shaped to strips by conventional extrusion molding method, they adhere to each other immediately after it has been extruded and become to a mass. Whereas, if the bean paste contains a moisture content lower than 25%, parts of extruded strips become masses, and in addition, on account of compression pressure required to the extrusion of such bean paste and amounting as high as several tens Kg/cm$^2$, liberated or isolated fatty substances ooze out over the surfaces of strip-formed paste, degenerating and browning products.

When bean paste of a moisture content of 33% is extruded into a vacuum chamber in accordance with this invention, vacuum of which chamber being about or less than 0.5 Torr, the paste of a room temperature of 25° C. is instantly cooled down to about −15° C., and vacuum evaporation effects the reduction of moisture content of said paste to about 30% or less than that. Thus obtained strip-like bean paste can maintain its forms, and could be granules without any adhesion among them by agitation or cutting them under vacuum.

While it shall be considered that the reduction of moisture content from 33% to #0%, viz., lowering of about 2 to 3% of moisture content is small, this small lowering of moisture content within the intermediate moisture content area is large enough to harden the materials even at a room temperature to such extent that the materials can not be extruded by a pressure having a double force. When such lowering is occurred under vacuum, vacuum cooling effects additionaly avoid the adhesion of materials to each other.

It shall be worthwhile to mention that when a block or plate-like bean paste having a thickness of about 2 cm is vacuum dried or vacuum frozen in order to reduce its moisture content from 100%–80% to 5%, viz., lowering of moisture content being 95% to 75%, time required for obtaining 60% to 70% of such lowering, viz., a moisture content thereof being about 30%, is about 1/6 of the total time required for obtaining 100% of the above lowering, viz., moisture content thereof being 5%. In other words, in order to obtain the remaining 30 to 40% of lowering, drying time is required as much as 5/6 of the total drying period of time. In view of this fact, and since materials of a moisture content of about 30% having aforementioned high drying efficiencies are granulated in this invention, the further reduction of moisture content of granules up to 5% can advantageously be made, because such granules can have larger contact surfaces, as repeatedly mentioned in the above. The time required for drying such granules up to 5% is about one third of the time required for drying the block or plate-shaped materials under the same conditions. Hence, the total time required for drying materials up to 5% in accordance with this invention shall be about a half of the time for drying the materials in block or plate shapes. Such advantageous reduction of time for drying operations can consequently reduce costs for the granulation of materials.

The above-mentioned effects are equally applicable in the drying and granulation of other paste-like, mushy and liquidous materials containing liquid constituents other than water such as alcohols and other organic solvents.

Compression pressures required in accordance with this invention for extruding materials of an intermediate moisture content which is higher than their plastic limit were tested with respect to bean paste as an example of the materials which can be advantageously granulated in accordance with this invention. Perforations through which the bean paste is extruded had respectively 1 mm in diameter, and extrusion pressures were selected between 10 Kg/cm$^2$ to 20 Kg/cm$^2$ which are easily practicable values in production.

When said perforation diameter and compression pressure are kept constant, but moisture contents of bean pastes are changed, extrusion reistances which are inverse functions of extrusion velocities and considerable as difficulties of molding or expressed commonly as hardness were changed as follows. In case of bean pastes having a moisture content from 40 to 31% which is a higher range of the aforementioned intermediate moisture content, compression pressures required for extruding such pastes changed at a rate of 1.23 times per on percent increase of moisture content. In case of pastes within a range of moisture contents from 30 to 27%, compression pressures required for the extrusion of such pastes were about 2.2 times per an increase of 1% of moisture content. When the pastes contain less than 27% moisture content, compression pressures required for extrusion of such pastes become larger. This means that irrespectively of the differences of moisture contents of materials, and provided that said moisture contents are within the intermediate moisture content area and higher their plastic limits, extrusion of pastes are possible under practically available pressures. In addition to the above advantages, the vacuum extrusion of materials having such moisture contents as defined above can harden also, on account of vacuum evaporation, about at five times in case of pastes having a moisture content from 31% to 29%, and about 1.5 times in case of pastes having a moisture content from 33% to 31%.

This invention involves the utilization of hardening of materials by vacuum cooling effects, also. Hardening of materials which could be expressed as extrusion resistances increases as follows. When a material of a room temperature of 20° C. to 24° C. is cooled to 0° C., hardening or extrusion resistance thereof increases by 10 times, and when said materials are cooled down as low as −10° C.-14° C., hardening or extrusion resistance becomes about 100 times. In the practice of this invention, double effects given by the easier lowering of moisture contents and by the vacuum cooling could expect hardening of the starting materials from several ten times to several hundred times, provided by a proper selection of vacuum pressures within a chamber in which the materials are extruded, and provided by the proper selection of a temperature of materials before the extrusion and after the extrusion under vacuum.

Taking as an example, in the extrusion of bean paste having the aforementioned properties, the paste could be of its moisture content in the order of thirty-odd %, by which sufficient hardening effects in accordance with this invention are obtainable by vacuum cooling. If a material could be controlled of its moisture content to the most appropriate percentage, for example, about 31 to 30% in case of bean paste, hardening of the material could be achieved primarily by the reduction of moisture content. Though physical properties of bean pastes differ or are not exactly same to each other, the above principles are applicable to bean pastes of various kinds, viz., of other moisture contents, and also to materials other than bean pastes, in which either one or both of the reduction of moisture contents and vacuum cooling attribute for advantageous granulation in accordance with this invention. Factors for achieving the granulation in accordance with this invention differ, depending upon physical properties of materials to be treated, but it is definite that the hardening of materials due to a difference of temperatures of materials before and after the extrusion could be larger when said difference be greater.

An apparatus which can be employed for achieving the method of this invention is explained hereinunder with reference to the drawing.

A vacuum chamber 1 having an exhaustion opening 7 is kept under vacuum by a vacuum pump, not illustrated, connected to said exhaustion opening 7. A degree of vacuum within the chamber has to be a pressure sufficiently lower than an equilibrium steam pressure of a low temperature which can prevent the adhesion of extruded strips of materials, for example lower than 4 Torr to 0.1 Torr. A cylinder 3 communicating with the chamber via a perforated plate 2 is provided with extrusion means 4. Though extrusion means illustrated in the drawing is consisted of a ram hydraulically or pneumatically operated, it can be a screw auger and so on. Materials are supplied continuously or intermittently into the cylinder 3 through a material supply inlet 5.

Mechanisms 6 for cutting or granulating the materials extruded in strips, comprise a propeller-like multi-blades 10 fixed to rotary shaft 9 and rotated by an electric motor 8 through said shaft, and a cylindrical screen 11 having meshes through which only granules of a desired size can pass. This screen shall have configurations other than a cylindrical shape, depending upon the nature of granules, and it shall not necessarily be provided within the chamber. Sizes of granules shall be decided, in this example, by factors including diameters of perforations of the perforated plate 2, shapes and rotary velocity of blades 10, and meshes of the screen 11.

When a considerable amount of air is expected to enter into the chamber 1 together with the supply of materials, air and vapours evaporated from the materials can be exhausted from the exhaustion opening 7. Or, alternatively, a separate exahustion outlet 12 would be provided to the cylinder 3, so that the cylinder can be preliminarily evacuated under vacuum, and so that capacity of the vacuum pump connected to the exhaustion opening 7 could be smaller.

Outlet 13 for discharging granules produced in the chamber and passed through the screen 11, is connected to a vacuum drying chamber 15 through a valve 14. If the granules produced in the chamber are taken out to atmosphere from said outlet 13 shortly or immediately after the granulation thereof, their temperature shall be of a room temperature by which granules might lose their extruded shapes. In order to avoid this fear, it is preferable to dry the granules in said chamber 15, especially when they are to be final products. Granules transferred into the vacuum drying chamber are kept under a low temperature on account of vacuum evaporation so far as they are wet and so far as said chamber is kept efficiently under vacuum. Irrespectively of the increase of temperature of granules with the progress of their dryness, they can keep granular forms because they are hardened by that time. The valve can be eliminated in case that the two chambers 1 and 15 are made as an unit chamber, and the granules can be continuously fallen into the chamber 15. However, if the production of granules is made on batch basis, a predetermined amount of granules have to be kept in the chamber 1, and then supplied into the chamber 15 through the opened valve 14. In this case, agitation screws may be provided in the chamber 1, so that blocking and other phenomena which adversely affect the granules on account of their heap within the chamber, can be prevented. Such agitation screw may be heated, or walls of the chamber 1 may be heated by steam jackets circumferentially provided to the walls, so that granules can dried to a desired extent by agitating and heating means of the above-mentioned kind, and so that they can be taken out from the outlet 13 directly to atmosphere.

When it is desired to use granules of an intermediate moisture content as intermediate products, they can be transferred from the outlet 13 to a next processing site, or be supplied to a hopper which is kept under a low temperature.

What is claimed is:

1. A method of granulating hydrated materials including food stuffs which comprises;
    processing said materials to a paste-like phase having
        an intermediate moisture content which is higher than the plastic limit of said processed materials, and which falls in the range of approximately 12–40% on a dry basis, extruding said materials through perforations to form them into strips, feeding the extruded strips into a vacuum chamber which is kept under a pressure lower than 4 Torr to 0.1 Torr, thereby hardening the extruded strips by means of rapid cooling of the extruded strips and reduction of the moisture content thereof by vacuum evaporation of said moisture content, and converting the strips to granules of a desired size by subjecting said strips to mechanical shearing forces under a vacuum.

2. Apparatus for granulating hydrated materials including food stuffs which comprises;

a chamber, means for connecting the chamber to a vacuum source to maintain the chamber under a vacuum lower than 4 Torr to 0.1 Torr, an inlet for feeding hydrated materials into said chamber, extrusion means connected to said chamber for extruding said materials through a first set of perforations and in strip form into said chamber, means provided in the chamber for granulating the strips of materials extruded through the first set of perforations, and a second set of perforations through which granules produced by said granulating means are disposed to pass upon discharge from said chamber.

3. Apparatus as defined in claim 2, wherein said granulating means comprises a plurality of cutting blades mounted in said chamber to rotate adjacent the discharge of said extrusion means, and said second set of perforations comprises a screen interposed between said blades and an outlet in said chamber to control the size of the granules discharged from said outlet.

4. Apparatus as defined in claim 3, wherein said blades rotate about a common axis, and said screen is cylindrical in configuration and surrounds said blades in said chamber.

* * * * *